United States Patent [19]

Hara

[11] Patent Number: 4,972,325
[45] Date of Patent: Nov. 20, 1990

[54] SIGNAL PROCESSING METHOD FOR DETERMINING BASE SEQUENCE OF NUCLEIC ACID

[75] Inventor: Makoto Hara, Minami-ashigara, Japan

[73] Assignee: Fuji Photo Film Co., Ltd., Minami, Japan

[21] Appl. No.: 31,841

[22] Filed: Mar. 30, 1987

[30] Foreign Application Priority Data

Mar. 29, 1986 [JP] Japan ................................ 61-71881

[51] Int. Cl.$^5$ ...................... G06F 15/20; G01N 33/58
[52] U.S. Cl. ............................... 364/497; 364/413.01; 364/496; 435/6
[58] Field of Search ................... 364/497, 496, 413.01, 364/413.13; 382/6; 435/6; 935/77; 358/111

[56] References Cited

U.S. PATENT DOCUMENTS

| | | |
|---|---|---|
| 4,665,312 | 5/1987 | Shiraishi et al. ............. 250/484.1 B |
| 4,720,786 | 1/1988 | Hara ................................. 364/413.01 |
| 4,777,597 | 10/1988 | Shiraishi et al. ............... 364/413.01 |
| 4,802,101 | 1/1989 | Hara ................................. 364/413.01 |
| 4,837,733 | 6/1989 | Shiraishi et al. ........................ 435/6 |

Primary Examiner—Parshotam S. Lall
Assistant Examiner—E. Ramirez
Attorney, Agent, or Firm—Sixbey, Friedman, Leedom & Ferguson

[57] ABSTRACT

A signal processing method for determining base sequence of nucleic acids by subjecting digital signals to signal processing, said digital signals corresponding to an autoradiograph of plural resolved rows which are formed by resolving a mixture of base-specific DNA fragments or base-specific RNA fragments labeled with a radioactive element in one-dimensional direction on a support medium,
which comprises steps of:
(1) preparing one-dimensional waveform composed of position along the resolving direction and signal level for each resolved row;
(2) dividing the one-dimensional waveform into at least two intervals; and
(3) smoothing the one-dimensional waveform in every interval through a smoothing means having different characteristics.

12 Claims, 3 Drawing Sheets

|   | a1  | a2  | a3  | a4  | a5  |
|---|-----|-----|-----|-----|-----|
| 1 | 1/5 | 1/5 | 1/5 | 1/5 | 1/5 |
| 2 | 0   | 1/4 | 1/4 | 1/4 | 1/4 |
| 3 | 0   | 1/3 | 1/3 | 1/3 | 0   |
| 4 | 0   | 0   | 1/2 | 1/2 | 0   |
| 5 | 0   | 0   | 1   | 0   | 0   |

SIGNAL PROCESSING METHOD FOR DETERMINING BASE SEQUENCE OF NUCLEIC ACID

BACKGROUND OF THE INVENTION

1. Field of the Invention

This invention relates to a signal processing method for determining base sequence of nucleic acids.

2. Description of the Prior Art

It is essential to obtain genetic information carried by organisms in order to make the function or replication mechanism of the organism clear in the field of molecular biology which has been rapidly developed in recent years. Particularly, it is essential to determine base sequence of nucleic acids such as DNA (or DNA fragment; the same applies hereinbelow) which carries specific genetic information.

Maxam-Gilbert method and Sanger-Coulson method are known as typical methods for determining the base sequence of nucleic acids such as DNA and RNA. In the former Maxam-Gilbert method, a group containing a radioactive isotope such as $^{32}P$ is attached to a chain molecule of DNA or a DNA fragment at one end to label it with the radioactive element and then the bond between the constitutional units of the chain molecule is base-specifically cleaved by a chemical reaction. A mixture of the resulting base-specific DNA cleavage products is resolved (developed) through gel electrophoresis to obtain a resolved pattern (not visible) wherein each of the numerous cleavage products is resolved on the gel support medium. The resolved pattern is visualized on a radiographic film such as an X-ray film to obtain an autoradiograph thereof as a visible image. The bases in certain positional relationships with the end of the radioactive element-attached chain molecule can be sequentially determined according to the visualized autoradiograph and the applied base-specific cleavage means. In this way, the sequence for all bases of the DNA specimen can be determined.

In the latter Sanger-Coulson method, synthetic DNA products which are complementary to the chain molecule of DNA or DNA fragment and radioactively labeled, are base-specifically synthesized by utilizing a chemical reaction, and the obtained mixture of numerous synthetic DNA products is resolved on a support medium by gel electrophoresis to obtain a resolved pattern. In a similar manner to that described above, the base sequence of DNA can be determined according to the visualized autoradiograph.

For the purpose of carrying out the determination of the base sequence of nucleic acids simply with high accuracy in autoradiography, there are described in U.S. patent applications No. 07/423,686 and No. 07/378,509 autoradiographic procedures which utilize a radiation image recording and reproducing method using a stimulable phosphor sheet, in place of the above-mensioned conventional radiography using a radiosensitive material such as an X-ray film. The stimulable phosphor sheet comprises a stimulable phosphor and has such properties that when exposed to a radiation, the stimulable phosphor absorbs a portion of radiation energy and then emits light (stimulated emission) corresponding to the radiation energy stored therein upon excitation with an electromagnetic wave (stimulating rays) such as visible light or infrared rays. According to this method, exposure time can be greatly shortened and there is no fear of causing problems such as chemical fog associated with prior arts. Further, since the autoradiograph having information on radioactively labeled substances is stored in the phosphor sheet as radiation energy and then read out as stimulated emission in time sequence, information can be expressed by the form of numerals and/or symbols in addition to image.

The base sequence of the nucleic acids has been conventionally determined by visually judging individual resolved positions of the base-specific cleavage products or the base-specific synthetic products of radioactively labeled nucleic acid (hereinafter referred as to simply base-specific fragments of nucleic acid) on the autoradiograph and comparing them among the resolved rows thereof. Namely, the analysis of the autoradiograph is done by observing the visualized autoradiograph with eyes, and such visual analysis requires great amounts of time and labor.

Further, since the visual analysis of the autoradiograph varies or fluctuates owing to the skill of investigators, the results on the determination of the base sequence of nucleic acid vary depending on the investigators and the accuracy of information is limited to a certain extent.

In order to improve the accuracy of the information, there are proposed in U.S. Pat. No. 4,777,597 and U.S. patent applications No. 07/161,248 (allowed), No. 06/917,606 and No. 06/917,609 methods for automatically determining the base sequence of DNA by obtaining the autoradiograph as digital signals and subjecting the digital signals to appropriate signal processing. The digital signals corresponding to the autoradiograph can be obtained either by visualizing the autoradiograph on a radiographic film and photoelectrically reading out the visible image on said film by means of reflected light or transmitted light when the conventional radiography is employed, or by directly reading out the stimulable phosphor sheet without the visualization of the autoradiograph when the radiation image recording and reproducing method is employed.

However, the resolved pattern obtained by resolving (developing) radioactively labeled substances on a support medium by electrophoresis or the like is liable to cause various distortion and noise. When the production and separation of the base-specific fragments are insufficient, or a sample is contaminated with radioactive impurities during the preparation of a sample, the digital signals corresponding to the autoradiograph contains noise. Further various noise is contained therein, when a stimulable phosphor sheet or a radiosensitive material is irradiated with a natural radiation during the exposure procedure, or when electric noise is produced in the conversion of the autoradiograph into the digital signals during the read-out procedure. Said noise, which is much smaller than a band (the width of a band), causes an error in the determination of band positions (peak positions of signal level). It is required to eliminate such fine noise simply and suitably prior to the signal processing in order to determine the base sequence of nucleic acids with high accuracy.

SUMMARY OF THE INVENTION

The present inventor has accomplished that the base sequence of nucleic acids is automatically determined with easiness and high accuracy by suitably processing digital signals corresponding to the autoradiograph.

The present invention provides a signal processing method for determining base sequence of nucleic acids by subjecting digital signals to signal processing, said digital signals corresponding to an autoradiograph of plural resolved rows which are formed by resolving a mixture of base-specific DNA fragments or base-specific RNA fragments labeled with a radioactive element in one-dimensional direction on a support medium, which comprises steps of:
(1) preparing one-dimensional waveform composed of position along the resolving direction and signal level for each resolved row;
(2) dividing the one-dimensional waveform into at least two intervals; and
(3) smoothing the one-dimensional waveform in every interval through a smoothing means having different characteristics.

According to the present invention, the fine noise can be suitably eliminated by subjecting the digital signals corresponding to the autoradiograph of a resolved pattern to processing (pre-processing) of smoothing signal levels, even when the digital signals contain noise.

There is generally a tendency that bands exist at a high density with narrow spaces therebetween in the upper part (zone near to the resolution-starting position) of the resolved pattern, and that bands exist sparsely with wide spaces therebetween toward the lower part (zone where the resolving distance is long) of the pattern. When the upper part of the resolved pattern is signalprocessed by smoothing on the same condition as that of the lower part thereof, peaks of signal levels become indistinct and the information on the base sequence of nucleic acids can not be accurately obtained.

According to the present invention, the resolved pattern is divided into several intervals in the resolving direction and the smoothing processing is conducted in every interval varying the processing condition suitably, whereby the digital signals can be smoothing-processed according to the band spaces (i.e., spaces between peaks of signal levels). The fine noise can be eliminated in the upper region of the pattern where the bands exist densely without losing the peaks, as well as the lower region.

After the smoothing processing, the bands are detected and sequenced among the resolved rows, and hence, the base sequence of nucleic acids can be determined simply with high accuracy.

DETAILED DESCRIPTION OF THE INVENTION

Figure 1:
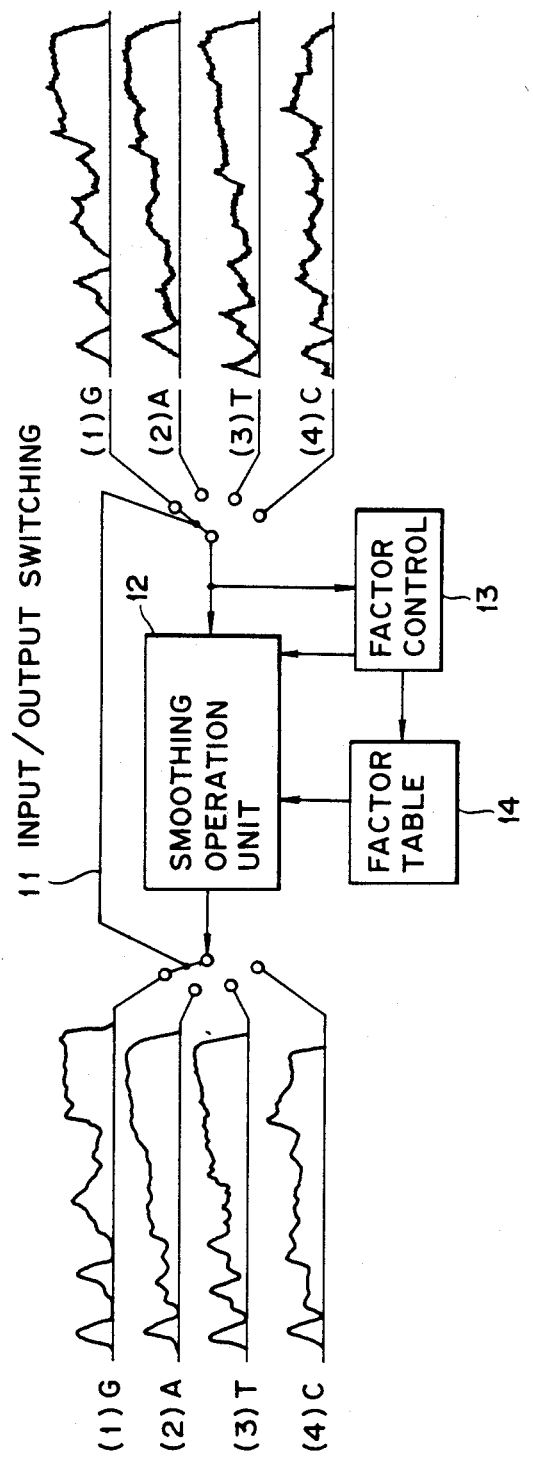
FIG. 1 schematically shows an example of a signal processing circuit for the smoothing processing according to the present invention.

Examples of samples employable in the present invention include mixtures of base-specific fragments of nucleic acids such as DNA and RNA labeled with a radioactive element. The term "fragments" of nucleic acids mean portions of a long-chain molecule. For instance, a mixture of base-specific DNA cleavage products, which is a kind of a mixture of base-specific DNA fragments, can be obtained by base-specifically cleaving the radioactively labeled DNA according to the aforementioned Maxam-Gilbert method. A mixture of base-specific DNA synthetic products can be obtained by synthesizing from radioactively labeled deoxynucleoside triphosphates and DNA polymerase by use of DNA as a template according to the aforementioned Sanger-Coulson method.

Mixtures of base-specific RNA fragments can be also obtained as a mixture of cleavage products or a mixture of synthetic products in the similar manner to the DNA methods. DNA is composed of four kinds of bases: adenine, guanine, thymine and cytosine as its constitutional units, and RNA is composed of four kinds of bases: adenine, guanine, uracil and cytosine. These substances can be labeled with a radioactive element such as $^{32}P$, $^{14}C$, $^{35}S$, $^{3}H$ or $^{125}I$ by any of appropriate methods.

A sample, which is a mixture of the base-specific fragments of a nucleic acid labeled with a radioactive element, can be resolved (developed) on a known support medium such as a gel support medium by any of conventional resolving (developing) procedures such as electrophoresis, thin layer chromatography, column chromatography and paper chromatography.

The support medium on which the radioactively labeled substances are resolved, is autoradiographed by means of the conventional radiography using a radiosensitive material or the radiation image recording and reproducing method using a stimulable phosphor sheet. The digital signals corresponding to the autoradiograph are then obtained through an appropriate read-out system.

When the conventional radiography is used, the support medium and a radiosensitive material such as an X-ray film are placed together in layers at a low temperature or at room temperature for a long period of time (several hours to several tens of hours) to expose the radiographic film. The radiographic film is then developed to visualize the autoradiograph of the radioactively labeled substances on the film, and the visualized autoradiograph is read out by using an image read-out system. For instance, the radiographic film is irradiated with an optical beam and the beam transmitted thereby or reflected therefrom is photoelectrically detected, whereby the visualized autoradiograph can be transformed to electric signals. Further, the electric signals are converted into digital signals corresponding to the autoradiograph through A/D conversion.

When the radiation image recording and reproducing method is used, the support medium and the stimulable phosphor sheet are placed together in layers at an ambient temperature for a short period of time (several seconds to several tens of minutes) to store radiation energy radiating from the radioactively labeled substances in the phosphor sheet, whereby the autoradiograph is recorded as a kind of a latent image (energy-stored image) on the phosphor sheet. The stimulable phosphor sheet, for instance, has a basic structure where a support comprising a plastic film, a phosphor layer comprising a stimulable phosphor such as a divalent europium activated barium fluorobromide phosphor ($BaFBr:Eu^{2+}$) and a transparent protective film are laminated in this order. The stimulable phosphor has characteristics of absorbing and storing radiation energy when irradiated with a radiation such as X-rays and subsequently releasing the stored radiation energy as stimulated emission when excited with visible light to infrared rays.

Then, the autoradiograph stored and recorded on the stimulable phosphor sheet is read out by using a read-out system. For instance, the phosphor sheet is scanned with a laser beam to release the radiation energy stored in the stimulable phosphor as light emission and the emitted light is photoelectrically detected, so that the autoradiograph can be directly obtained as electric signals without the visualization thereof. Further, the electric signals are converted into digital signals corresponding to the autoradiograph through A/D conversion.

The above-described methods for measuring the autoradiograph and obtaining the digital signals corresponding thereto are described in more detail in the aforementioned U.S. Pat. No. 4,777,597 and U.S. patent applications No. 07/378,509.

While the methods for obtaining the digital signals corresponding to the autoradiograph using the conventional radiography and the radiation image recording and reproducing method are described above, the present invention is not limited thereto and digital signals obtained by any other methods can be applied to the signal processing method of the invention, provided that they correspond to the autoradiograph.

In the above read-out procedures, it is not always necessary to conduct the read-out operation of the autoradiograph all over the surface of the radiographic film or the stimulable phosphor sheet. Only the image region may be subjected to the read-out operation.

In the present invention, there may be previously inputted information on the location of each resolved row and the width of band to preset read-out conditions and then conducted scanning at a scanning line density such that each band is traversed by at least one scanning lines in the read-out operation, so as to shorten readout time and obtain efficiently necessary information. The digital signals corresponding to the autoradiograph in the invention also include the thus-obtained digital signals.

The obtained digital signals $D_{xy}$ comprise a coordinate (x,y) which is represented by a coordinate system fixed to the radiographic film or the stimulable phosphor sheet and a signal level (z) at the coordinate. The signal level represents the density of image at the coordinate, that is, the amount of the radioactively labeled substances. Accordingly, a series of the digital signals (namely, digital image data) have information on two-dimensional location of the labeled substances.

The digital signals corresponding to the autoradiograph of the radioactively labeled substances resolved on a support medium, is subjected to signal processing to determine the base sequence of nucleic acid according to the invention described in more detail below.

Now, the signal processing method of the present invention will be described by referring to an example of an electrophoretic pattern formed with a combination of the following four groups of base-specific DNA fragments labeled with a radioactive element:
(1) guanine (G)—specific DNA fragments,
(2) adenine (A)—specific DNA fragments,
(3) thymine (T)—specific DNA fragments,
(4) cytosine (C)—specific DNA fragments.

Each group of the base-specific DNA fragments is composed of base-specific cleavage products or synthetic products which have various lengths and the same base at terminals.

The digital signals corresponding to the autoradiograph are stored temporarily in a memory device of the signal processing circuit (that is, stored in a nonvolatile memory unit such as a buffer memory, a magnetic disk, etc.).

In the first place, there is prepared one-dimensional waveform composed of position along the resolving direction and signal level for each resolved row (lane).

The one-dimensional waveforms prepared for the first to fourth lanes are shown on the right side of FIG. 1.

In the second place, each of the one-dimensional waveforms is subjected to the smoothing processing.

FIG. 1 schematically shows an example of the signal processing circuit for the smoothing processing according to the present invention. In FIG. 1, the signal processing circuit comprises input/output switching 11, smoothing operation unit 12, factor control 13 and factor table 14. The digital signals inputted to the signal processing circuit in the form of one-dimensional waveforms, as shown on the right side of FIG. 1, are sequentially transmitted to the smoothing operation unit 12 for each lane by switching from a lane to another lane in the input/output switching 11. The factor control 13 detects the input signals transferred to the smoothing operation unit 12, and sends a signal of factor change to the smoothing operation unit 12 at each time when the number of the detected signals exceeds K, (wherein K=N/M, N being the number of signals per lane and M being the number of divided intervals), and at the same time sends a signal of factor output to the factor table 14. When the factor table 14 accepts the signal of factor output, the factor table sends a factor which is previously set for each interval to the smoothing operation unit 12. When the smoothing operation unit 12 accepts the signal of factor change from the factor control unit 13 and the factor from the factor table 14, the operation unit executes the smoothing operation on the transmitted signals according to said factor. The operation-processed signals are outputted for each waveform by the input/output switching 11. Thus, one-dimensional waveforms smoothing-processed are obtained, as shown on the left side of FIG. 1.

As for the smoothing means, there are employed in the invention various known noise reduction filters for eliminating noise contained in digital signals. Examples of the smoothing means include a moving average filter, a weighted mean filter and a filter having low-pass characteristics.

The smoothing processing according to the present invention will be described by referring to an example using the moving average filter.

The one-dimensional waveform of each lane is divided into plural intervals. For example, the one-dimensional waveform is divided into eight blocks so as to be about 5 cm per interval, when the whole electrophoretic pattern is approx. 40 cm long.

Figure 2:
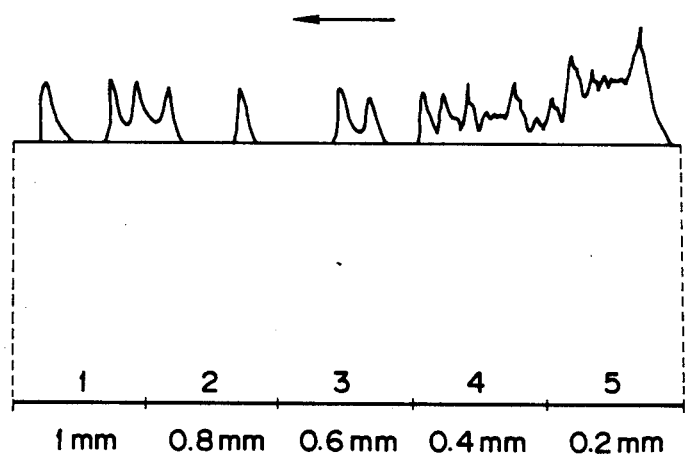
FIG. 2 shows an example of a one-dimensional waveform, interval division and mask sizes.

FIG. 2 shows an example of the one-dimensional waveform having a whole length of approx. 25 cm and the interval division thereof. In FIG. 2, the electrophoretic direction is the direction of an arrow (←) and the one-dimensional waveform is divided into five blocks.

The electrophoretic pattern has bands the spaces of which (i.e., peaks of signal levels) are gradually sparse as the migration distance is long, as shown in FIG. 2. Mask size of the moving average filter is set in such a manner as to become small step by step from the lower end of the electrophoresis toward the upper end, as shown on the lower side of FIG. 2. The mask size means unit of the moving average operation (filtering). For example, when the size of a pixel to which one signal corresponds is 200 μm, five signals are contained in one mask of the first interval (where the mask size is 1 mm) and the operation processing gives a result of five point average. The results of five point, four point, three point, two point and one point averages are respectively obtained for the first to fifth intervals according to the mask sizes.

Figure 3:
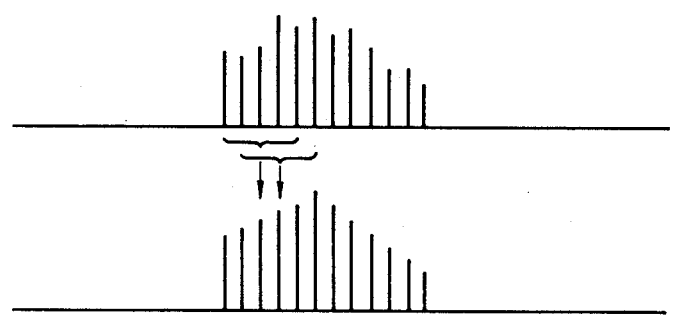
FIG. 3 shows an example of five point average.

FIG. 3 shows an example of the five point average.

Figures 4, 5:
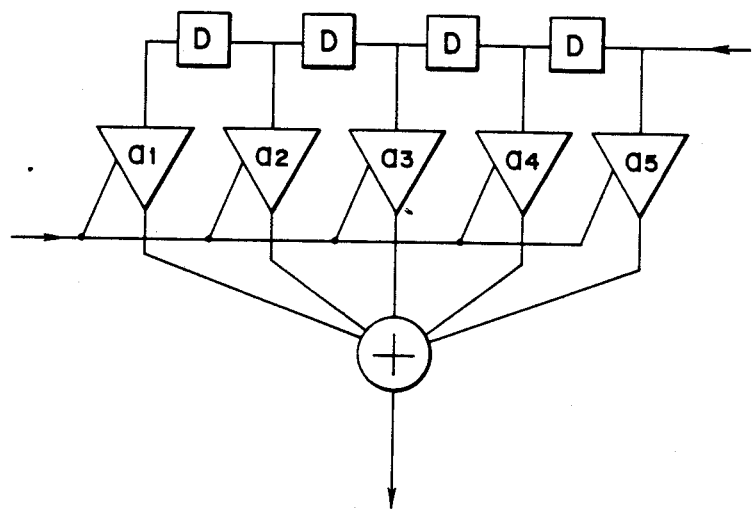
FIG. 4 shows an example of factor table.
FIG. 5 schematically shows an example of a smoothing operation unit.

FIG. 4 shows an example of the factor table and FIG. 5 schematically shows an example of the smoothing operation unit.

The factor table of FIG. 4 is inputted and set in the factor table 14 within the signal processing circuit of FIG. 1. For example, the filter factors for the first interval are $a_i=1/5$ (wherein i=1-5) owing to the five point average, and the filter factors for the fifth interval are $a_3=1$ and $a_i=0$ (wherein i=1, 2, 4, 5) owing to the one point average.

In the smoothing operation (moving average operation) unit 12, as shown in FIG. 5, the signals inputted from the direction of an arrow (→) on the right side of FIG. 5 are subjected via one-sample delay D to the following operation according to the factor $a_i$ (wherein i=1-5) inputted from the direction of another arrow (←) on the left side of FIG. 5:

$$S(n) = \sum_{j=n-2}^{n+2} a_i S(j)$$

wherein S(j) and S(n) are digital signals, $a_i$ is a factor and j and n are positive integers within a range of 1 to N. The processed signals are outputted from the other arrow (↓) on the lower side of FIG. 5.

In this way, the filtering is made varying the mask size for each interval. Namely, the filter having a large mask size is employed in the lower part of the electrophoretic pattern to have much effect of the noise reduction. On the other hand, the filter having a relatively small mask size is employed in the upper part of the pattern, so that the noise reduction effect is not much and the peaks are remained without becoming indistinct.

The smoothing-processed digital signals are further subjected to appropriate signal processing so that bands are detected on each lane and sequenced.

The signal processing for the detection and the sequencing of the bands can be conducted according to methods of processing digital signals while making various correction, which have been filed for patent applications by the present inventor. For instance, there are methods of determining the base sequence of nucleic acids while correcting a smiling phenomenon or various distortions such as offset distortion and combining of some bands, or eliminating noise such as extra band.

The smiling phenomenon is a phenomenon in which migration distances of the radioactively labeled substances at the both sides of the support medium are shorter than that in the vicinity of the center thereof. The smiling phenomenon is caused by heat dissipation effect (so-called edge effect), etc. during the electrophoresis. The offset distortion is a phenomenon in which positions of the lanes are wholly deviated from one another and is caused by difference between the slots in the electrophoresis-starting position or time of samples, which is due to the unevenness of the shapes of slots, etc. The combining of bands is a phenomenon in which two or three bands are combined together to form one broad band and is caused by the insufficient electrophoresis. Usually, the combined bands tend to be appeared in the upper region of the pattern near to the electrophoresistarting position.

These signal processing methods are described in our co-pending Japanese Patent Application Nos. 60(1985)-74899, 60(1985)-74900, 60(1985)-85275, 60(1985)-85276, 60(1985)-111185, 60(1985)-111186 and 61(1986)-69074 (the whole content of which corresponds to U.S. Pat. No. 4,720,786 and U.S. patent applications No. 06/849,187, No. 06/866,355 (allowed) and No. 07/030,062 (allowed).

The band sequence can be easily determined by utilizing the fact that there do not exist two or more bands at the corresponding positions on different lanes, since the combination of the above four groups of the base-specific DNA fragments is exclusive. Since the slots (1) to (4) have information on the terminal bases of (G), (A), (T) and (C), respectively, the base sequence of DNA is obtained by substituting the bands with bases corresponding to the slots which the individual bands belong to. For instance, the following base sequence of DNA can be obtained.

A - G - C - T - A - A - G - . . .

Thus, the base sequence of one chain molecule of DNA can be determined. The representation mode of the information on the base sequence of DNA is by no means limited to the above-mentioned mode, and other representation modes may be utilized. For instance, the intensity (z') of each band can be represented as the relative amount of the radioactively labeled substances, if desired. Further, the base sequence of both two chain molecules of DNA can be also represented.

Information on the base sequence of DNA can be also displayed as an image on the basis of the above processed digital signals. At the same time, the original autoradiograph can be displayed as a visible image. In this case, investigators themselves can finally determine the DNA sequence on the basis of the display image.

In the above-mentioned example, there has been described the case where the exclusive combination of the mixture (G, A, T, C) of base-specific DNA fragments as a sample is used, but the signal processing method of the present invention is by no means limited to said combination, and other combinations can be used. For instance, a combination of (G, G+A, T+C, C) may be used. Further, the method of the invention can be also applied to the mixtures (for instance, a combination of G, A, U, C) of base-specific RNA fragments. The smoothing of digital signals is not limited to resolved rows of one combination of base-specific fragments of a nucleic acid, but can be made for the whole resolved rows simultaneously resolved on a support medium.

It is possible to perform the genetic philological information processing such as comparison between the obtained base sequence of the DNA and the base sequence of another DNA which has been already recorded and stored in a suitable means.

The information on the base sequence of DNA determined through the above-described signal processing is output from the signal processing circuit and subsequently transmitted to a recording device directly or optionally via storage in a storing means such as a magnetic disk or a magnetic tape.

Various recording devices based on various systems can be employed for the above-described purpose, for instance, a device for visualizing optically by scanning a photosensitive material with laser beam, etc., a display means for visualizing electrically on CRT, etc., a means for printing a radiation image displayed on CRT by means of a video printer, and a means for visualizing on a heatsentitive recording material using thermic rays.

I claim:

1. A signal processing method for determining base sequence of nucleic acids by subjecting to signal processing digital signals corresponding to an autoradiograph of plural resolved rows which are formed by resolving a mixture of base-specific DNA fragments or base-specific RNA fragments labeled with a radioactive element in a one-dimensional resolving direction on a support medium, which comprises the steps of:
   (1) generating a one-dimensional waveform composed of position along the resolving direction and signal level for each resolved row;
   (2) selecting at least two intervals along the one-dimensional waveform;
   (3) subjecting the digital signals in each said interval to smoothing processing using a moving average filter having a mask size that is varied for each said interval; and
   (4) subjecting the smoothing processed digital signals to further processing, thereby detecting and sequencing bands corresponding to the sequence of bases in said nucleic acids.

2. The signal processing method as claimed in claim 1, wherein the mask size of said moving average filter is varied in every interval in the step (3).

3. The signal processing method as claimed in claim 2, wherein the mask size of said moving average filter is enlarged as the resolving distance is long in the step (3).

4. The signal processing method as claimed in claim 1, wherein said mixture of the base-specific DNA fragments consists of the four groups of:
   (1) guanine-specific DNA fragments;
   (2) adenine-specific DNA fragments;
   (3) thymine-specific DNA fragments; and
   (4) cytosine-specific DNA fragments; and the resolved rows consist of four rows formed by resolving each of said four groups of the base-specific DNA fragments on the support medium.

5. The signal processing method as claimed in claim 1, wherein said digital signals corresponding to the autoradiograph are obtained by placing the support medium and a stimulable phosphor sheet comprising a stimulable phosphor together in layers to record the autoradiograph of the resolved rows on the phosphor sheet as an energy-stored image, irradiating said phosphor sheet with stimulating rays and photoelectrically detecting the autoradiograph as stimulated emission.

6. The signal processing method as claimed in claim 1, wherein said digital signals corresponding to the autoradiograph as obtained by placing the support medium and a radiosensitive material together in layers to record the autoradiograph of the resolved rows on the radiosensitive material as a visible image and photoelectrically reading out the autoradiograph visualized on said radiosensitive material.

7. A signal processing method for determining base sequence of nucleic acids by subjecting to signal processing digital signals corresponding to an autoradiograph of plural resolved rows which are formed by resolving a mixture of base-specific DNA fragments or base-specific RNA fragments labeled with a radioactive element in a one-dimensional resolving direction on a support medium, which comprises the steps of:
   (1) generating a one-dimensional waveform composed of position along the resolving direction and signal level for each resolved row;
   (2) selecting at least two intervals in the resolving direction along the one-dimensional waveform thus generated;
   (3) processing each of said intervals with a smoothing means for smoothing processing the digital signals in each said interval according to spaces of bands in each said interval;
   (4) detecting the sequence of bands in each resolved row; and
   (5) determining said base sequence from the detected band sequence.

8. The signal processing method as claimed in claim 7, wherein said smoothing means is a weighted mean filter in the step (3).

9. The signal processing method as claimed in claim 7, wherein said smoothing means is a filter having low-pass characteristics in the step (3).

10. The signal processing method as claimed in claim 7, wherein said mixture of the base-specific DNA fragments consists of the four groups of:
    (1) guanine-specific DNA fragments;
    (2) adenine-specific DNA fragments;
    (3) thymine-specific DNA fragments; and
    (4) cytosine-specific DNA fragments; and the resolved rows consist of four rows formed by resolving each of said four groups of the base-specific DNA fragments on the support medium.

11. The signal processing method as claimed in claim 7, wherein said digital signals corresponding to the autoradiograph are obtained by placing the support medium and a stimulable phosphor sheet comprising a stimulable phosphor together in layers to record the autoradiograph of the resolved rows on the phosphor sheet as an energystored image, irradiating said phosphor sheet with stimulating rays and photoelectrically detecting the autoradiograph as stimulated emission.

12. The signal processing method as claimed in claim 7, wherein said digital signals corresponding to the autoradiograph are obtained by placing the support medium and a radiosenstive material together in layers to record the autoradiograph of the resolved rows on the radiosensitive material as a visible image and photoelectrically reading out the autoradiograph visualized on said radiosensitive material.

* * * * *